US009522121B2

(12) United States Patent
Anton et al.

(10) Patent No.: US 9,522,121 B2
(45) Date of Patent: Dec. 20, 2016

(54) AQUEOUS-CORE LIPID NANOCAPSULES FOR ENCAPSULATING HYDROPHILIC AND/OR LIPOPHILIC MOLECULES

(75) Inventors: Nicolas Anton, Angers (FR); Patrick Saulnier, Marigne (FR); Jean-Pierre Benoit, Angers (FR)

(73) Assignee: UNIVERSITE D'ANGERS, Angers (FR)

( * ) Notice: Subject to any disclaimer, the term of this patent is extended or adjusted under 35 U.S.C. 154(b) by 295 days.

(21) Appl. No.: 12/678,868

(22) PCT Filed: Sep. 18, 2008

(86) PCT No.: PCT/EP2008/062435
§ 371 (c)(1),
(2), (4) Date: Aug. 9, 2010

(87) PCT Pub. No.: WO2009/037310
PCT Pub. Date: Mar. 26, 2009

(65) Prior Publication Data
US 2010/0297247 A1  Nov. 25, 2010

(30) Foreign Application Priority Data
Sep. 18, 2007 (EP) .................................. 07291109

(51) Int. Cl.
| A61K 9/16 | (2006.01) |
| A61K 9/50 | (2006.01) |
| A61K 9/51 | (2006.01) |
| A61K 8/11 | (2006.01) |
| A61K 8/87 | (2006.01) |
| A61K 9/107 | (2006.01) |
| A61Q 19/00 | (2006.01) |
| B01J 13/16 | (2006.01) |

(52) U.S. Cl.
CPC .............. *A61K 9/5146* (2013.01); *A23P 10/30* (2016.08); *A23P 10/35* (2016.08); *A61K 8/11* (2013.01); *A61K 8/87* (2013.01); *A61K 9/1075* (2013.01); *A61Q 19/00* (2013.01); *B01J 13/16* (2013.01); *A61K 2800/412* (2013.01); *A61K 2800/413* (2013.01)

(58) Field of Classification Search
CPC ...... A61K 9/51; A61K 9/5138; A61K 9/5176; A61K 9/5123; A61K 9/5107; A61K 9/5146; A61K 9/5192
USPC .................................................. 424/488–501
See application file for complete search history.

(56) References Cited

U.S. PATENT DOCUMENTS

| 5,925,364 A * | 7/1999 | Ribier .................. A61K 8/0295 424/401 |
| 6,017,559 A * | 1/2000 | Mulqueen et al. ........... 424/451 |
| 2002/0155084 A1* | 10/2002 | Roessler et al. ............ 424/70.21 |
| 2004/0115254 A1* | 6/2004 | Niedzinski et al. ........... 424/450 |
| 2005/0028520 A1* | 2/2005 | Chertok .................. F02G 1/043 60/517 |
| 2006/0078520 A1* | 4/2006 | Pays et al. .................... 424/70.7 |
| 2006/0127490 A1* | 6/2006 | Wu et al. ....................... 424/490 |
| 2007/0154560 A1* | 7/2007 | Hyon ............................ 424/489 |

FOREIGN PATENT DOCUMENTS

| WO | 03086609 A1 | 10/2003 |
| WO | 2004112695 A2 | 12/2004 |
| WO | 2007083316 A2 | 7/2007 |

OTHER PUBLICATIONS

Hilaireau H, et al; Encapsulation of mono and oligo nucleotides into aqueous-core nanocapsules in presence of various water-solbel polymers, 2007, International Journal of Pharmaceuticals, 331, 148-152. XP-002462563.*
Hillaireau et al, Encapsulation of mono- and oligo-nucleotides into aqueous-core nanocapsules in presence of various water-soluble polymers, 2007, International Journal of Pharmaceutical, 331, 148-152.*
"The Merck Index", 2001, pp. 474-475; example 2752 & pp. 573; example 3285, Merck & Co., Inc., USA, XP002468453
Bouchemal et al., "Synthesis and Characterization of Polyurethane and Poly (Ether Urethane) Nanocapsules Using a New Technique of Interfacial Polycondensation Combined to Spontaneous Emulsification", International Journal of Pharmaceutics, 2004, pp. 89-100. vol. 269.
Cho et al., "Microencapsulation of Octadecane as a Phase-Change Material by Interfacial Polymerization in an Emulsion System", Colloid Polym Sci., 2002, pp. 260-266, vol. 280.
Crespy et al., "Polymeric Nanoreactors for Hydrophilic Reagents Synthesized by Interfacial Polycondensation on Miniemulsion Droplets". Macromolecules, 2007, pp. 3122-3135, vol. 40, No. 9.
Ganachaud et al., "Nanopanicies and Nanocapsules Created Using the Ouzo Effect Spontaneous Emulsification as an Alternative to Ultrasonic and High-Shear Devices", ChemPhysChem, 2005, pp. 209-216. vol. 6.
Hillaireau et al., "Encapsulation of Mono- and Oligo-Nucleotides into Aqueous-Core Nanocapsules in Presence of Various Water-Soluble Polymers", International Journal of Pharmaceuticals, Oct. 27, 2006, pp. 148-152, vol. 331.
Lambert et al., "Polyisobutylcyanoacryiate Nanocapsules Containing an Aqueous Core for the Delivery of Oligonucleotides", International Journal of Pharmaceutics, 2001, pp. 13-16, vol. 214.
Landfester, "Synthesis of Colloidal Particles in Miniemulsions", Annu. Rev. Mater. Res., 2006, pp. 231-279, vol. 36.
Montasser et al., "The Effect of Monomers on the Formulation of Polymeric Nanocapsules Based on Polyureas and Polyamides", International Journal of Pharmaceutics, Nov. 10, 2006, pp. 176-179, vol. 335.

(Continued)

*Primary Examiner* — Micah-Paul Young
(74) *Attorney, Agent, or Firm* — Thompson Coburn LLP

(57) ABSTRACT

The invention relates to a composition comprising in an aqueous phase, particles having a diameter in the range of 20 to 500 nm, said particles containing:—an oil phase;—in said oil phase,—an aqueous droplet, or—a nanocapsule (NC) comprising:—an aqueous core, and—a polymeric shell or a shell composed of an amphiphilic substance; and—a surfactant. This composition is particularly useful for encapsulating hydrophilic and/or lipophilic substances.

25 Claims, 8 Drawing Sheets

(56) References Cited

OTHER PUBLICATIONS

Figure 1:
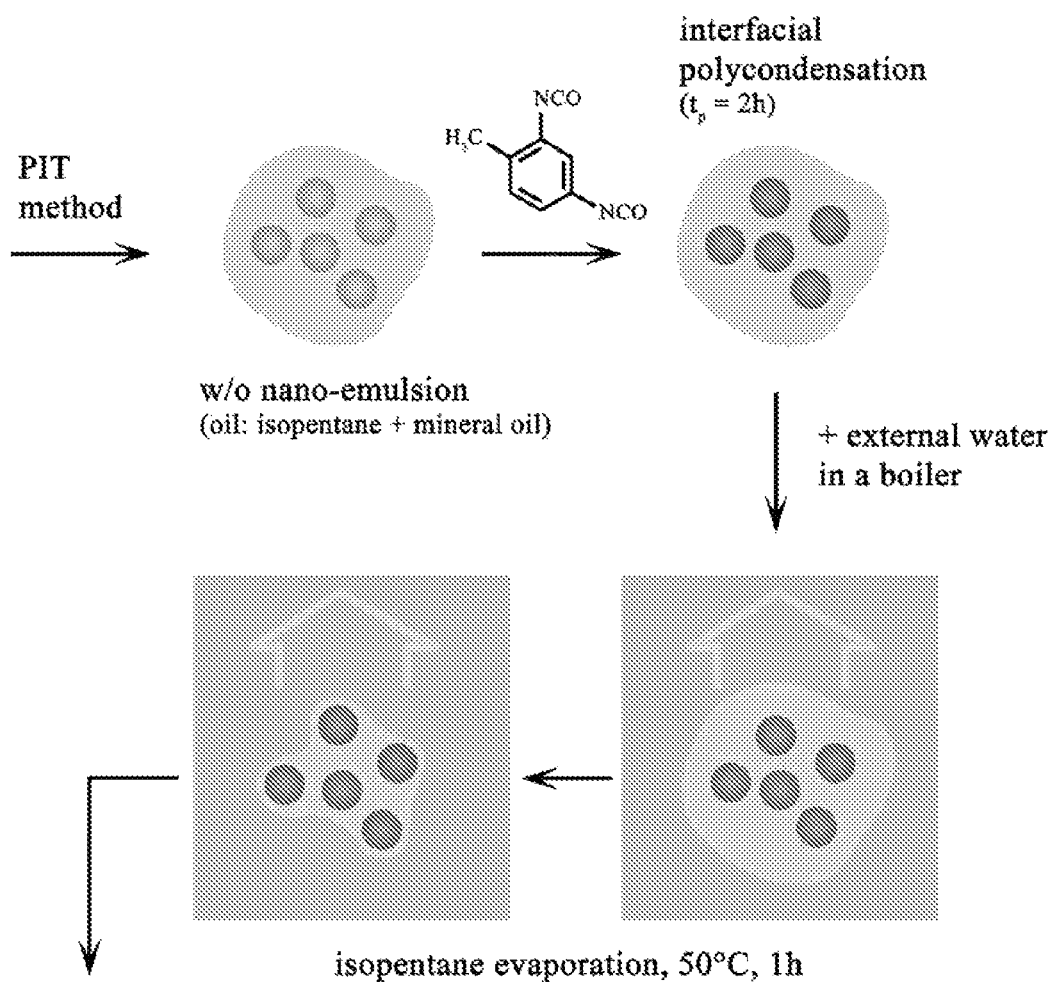

Paiphansiri et al., "Polymeric Nanocapsules Containing an Antiseptic Agent Obtained by Controlled Nanoprecipitation onto Water-in-Oil Miniemulsion Droplets", Macromolecular Bioscience, 2006, pp. 33-40, vol. 6.

Pitaksuteepong et al., "Factors Influencing the Entrapment of Hydrophilic Compounds in Nanocapsules Prepared by Interfacial Polymerisation of Water-in Oil Microemulsions", European Journal of Pharmaceutics and Biopharmaceutics, 2002, pp. 335-342, vol. 53.

International Search Report and Written Opinion of corresponding PCT Application No. PCT/EP2008/062435 dated Dec. 22, 2009, 18 pages.

* cited by examiner

AQUEOUS-CORE LIPID NANOCAPSULES FOR ENCAPSULATING HYDROPHILIC AND/OR LIPOPHILIC MOLECULES

CROSS-REFERENCE TO RELATED APPLICATIONS

This application is a National Stage application of International Patent Application No. PCT/EP2008/062435, filed on Sep. 18, 2008 and incorporated herein in its entirety, which claims the benefit of European Application No. 07291109.2 filed Sep. 18, 2007.

The invention relates to novel compositions comprising aqueous core lipid nanocapsules, their method of preparation and their use for the encapsulation of hydrophilic and/or lipophilic molecules.

Nanocapsules (NC) are overall described as colloidal objects that exhibit a core-shell structure, the core acting as a liquid reservoir for drugs, and the shell as protective membrane. NC systems have been shown for the last decades, not only to be very promising potential carriers for drug delivery but also to be very interesting colloids of therapeutic and diagnosis applications, e.g. as contrast agent. The strong advantages of such drug carriers with regards to the conventional nanospheres and nanoparticles, appear in the following points: (i) the high drug encapsulation efficiency due to the optimized drug solubility into the nanoparticle core; (ii) a significantly reduced polymer content compared to polymeric nanospheres; and (iii) the drug to be encapsulated may be considered to be 'protected' within the NC core, protecting also the drug itself from potential degradation.

The two fundamentally different kinds of NC are defined following the nature of the materials constituting their liquid core, that is, either oil- or aqueous-core nanocapsules, and both dispersed in a water continuous phase. Actually, it is the former sort (oil-core NC) that constitutes the most widely encountered systems, owing to their easier formulation ways in water bulk phase, generally from oil-in-water nanoemulsions systems to either in situ interfacial polymer shell synthesis or nanoprecipitation of preformed polymers.

However, these oil-core NC systems will only result useful for the encapsulation of lipophilic species, and so, in order to encapsulate hydrophilic ones, many efforts are dedicated for the last years (as the current study), to the generation of aqueous-core nanocapsules dispersed in an aqueous bulk phase. Different strategies have been undertaken in that sense, from the interfacial polymerization of inverted finely dispersed emulsions (Lambert, G. et al., 2000; Lambert, G. et al., 2000) or water-in-oil microemulsions (Hillaireau, H. et al., 2006) to alternative processes consisting of the stabilization of liposomes by in situ polymerization between lipids, forming aqueous-core polymerosome nano-structures (Ruysschaert T. et al., 2006; Gomes, J. F. P. d. S. et al., 2006).

It now has been developed a method for preparing nanoassemblies forming aqueous-core reservoir nanocapsules, generated from water-in-oil nano-emulsions template, notably by low-energy methods, and giving rise to novel multifunctional objects that are also composed of oil reservoir which is the nanocapsule shell.

These aqueous core nanocapsules are particularly useful for the encapsulation and the delivery of hydrophilic or lipophilic species, notably of fragile drugs. Further, they also offer the particular advantage of enabling simultaneously the encapsulation of hydrophilic species in the aqueous core and of lipophilic species in the lipid shell with high yields.

Thus, according to a first object, the invention relates to a method for preparing a composition comprising in an aqueous phase, particles (P) having a diameter in the range of 20 to 500 nm, said particles containing:
an oil phase;
in said oil phase,
  an aqueous droplet, or
  a nanocapsule (NC) comprising:
    an aqueous core, and
    a polymeric shell or a shell composed of an amphiphilic substance;
  and
a surfactant;
said method comprising the steps of:
i) preparing a water-in-oil (w/o) emulsion ($E_1$) wherein droplets have a mean hydrodynamic diameter of 10 to 400 nm, wherein the continuous phase contains two oils, a volatile ($O_1$) and a non volatile oil ($O_2$), the volatile oil ($O_1$) being more volatile than water, and the non volatile oil ($O_2$) being less volatile than water;
ii) optionally forming aqueous shell—core nanocapsules (NC) either by adding a monomer which is soluble in the continuous phase of the emulsion ($E_1$) and which polymerizes when in contact with water, or by adding an amphiphilic substance; and
iii) adding a water phase and removing the volatile oil ($O_1$), thereby forming the desired composition.

As used herein, the term "mean diameter" refers to the sum of the size measurements of all measurable particles measured divided by the total number of particles measured.

The "hydrodynamic mean diameter" of the droplets of the emulsion $E_1$ according to the invention (also referred to herein as "nanoemulsion") is determined by virtue of a particle size measurement performed on the emulsion according to the method based on Dynamic Light Scattering.

The diameter of the particles (P) is determined by virtue of a particle size measurement performed on Transmission Electron Microscopy (TEM) and/or on Cryo-TEM.

Step i)

The water-in-oil (w/o) emulsion ($E_1$) comprises water as a discontinuous phase, a mixture of two oils ($O_1$) and ($O_2$) as a continuous phase, and a surfactant. It may be prepared according to any conventional techniques known in the art, including notably the so-called high-energy methods that involve high-shear devices such as high pressure homogenizers or sonifiers, and the low-energy methods such as the spontaneous emulsification (or solvent diffusion) and the phase inversion temperature (PIT) method.

Among these, low energy methods, and more particularly the PIT method, are preferred, notably for drug encapsulation, as they may prevent the degradation during processing of the fragile molecules to be encapsulated.

The PIT method is an organic solvent-free method introduce for thirty years by Shinoda and Saito (Shinoda, K. et al., 1968; Shinoda, K. et al., 1969), and which has been essentially reported for the preparation of oil-in-water emulsions. This method consists in stabilizing water/oil emulsion by a thermo-sensitive nonionic surfactant, which sees its own solubility for the two immiscible phases varying as a function of the temperature. In that way, the whole macroemulsions undergo a transitional phase inversion, when at fixed composition, a temperature gradual change is applied to the sample. Then, a water-in-oil (w/o) emulsion will become an oil-in-water (o/w) one, following an increase of the sample temperature, and vice versa with a decrease. At the phase inversion temperature (PIT), the affinities of the surfactants for water and oil are balanced, resulting in the establishment of bicontinuous microemulsions, nanometric-scale structured.

Therefrom, the 'PIT method', applied to the preparation of oil/water emulsions, assimilated to an irreversible process forming kinetically stable nanoemulsions droplets, consists in suddenly breaking-up such a bicontinous nanometric network by performing at the PIT, a rapid cooling and/or a sudden water dilution.

The inventors have recently developed a method based on the PIT method, which has been modified and adapted for generating the nanoemulsions in oil continuous phase. Mainly, the process is divided-up into ($i_1$) a stage of temperature cycling around the PIT, and ($i_2$) a stage of sudden dilution for breaking-up the transitional microemulsion structure immediately generating nano-emulsions. Thus, when this step is usually performed by water dilution for creating o/w nanoemulsions, the transitional microemulsion is suddenly diluted with oil, leading to the formation of w/o nanoemulsion.

Thus, according to a preferred embodiment, the (w/o) emulsion ($E_1$) is prepared according to the PIT method and comprises a surfactant ($S_1$), which is more soluble in the non volatile oil ($O_2$) than in water when the temperature is superior to the phase inversion temperature (PIT) and more soluble in water than in the non volatile oil ($O_2$) phase when the temperature is inferior to the PIT.

More specifically, the water-in-oil (w/o) emulsion ($E_1$) is prepared according to a method comprising the steps of:

$i_1$) forming a nanostructured bicontinuous system from a ternary mixture comprising:
the non volatile oil ($O_2$);
the water; and
the surfactant ($S_1$)
by carrying out a temperature cycling around the PIT;

$i_2$) forming a w/o emulsion wherein droplets have a hydrodynamic mean diameter in the range of 10 to 400 nm by adding the volatile oil ($O_1$); and $i_3$) optionally adding a further amount of a surfactant ($S_2$).

As used herein, the terms "volatile oil" means an oil that is more volatile than water, that is an oil which has a boiling point inferior to that of water and notably inferior to 50° C., preferably comprised in the range of 25° C. and 50° C. Examples of volatile oils suitable for the preparation of a nanoemulsion according to step i) are notably isopentane ($B_p$=28° C.) or pentane ($B_p$=36° C.).

As used herein, the terms "non volatile oil" means an oil which is less volatile than water, that is having a boiling point superior to that of water, preferably superior to 150° C.

Preferably, the non volatile oil ($O_2$) is pharmaceutically acceptable.

As used herein "pharmaceutically acceptable" refers to those oils which are, within the scope of sound medical judgement, suitable for contact with the tissues of human beings and animals without excessive toxicity, irritation, allergic response, or other problem complications commensurate with a reasonable benefit/risk ratio.

Preferably, the non volatile oil ($O_2$) is a so-called 'light mineral oil' which is a standardized denomination to refer to a mixture of saturated hydrocarbons obtained from petroleum and which is advantageously pharmaceutically acceptable.

Preferably, the volume ratio of $O_1/O_2$ is superior to 1, notably to 3 and more particularly to 5.

Preferably, the phase inversion temperature (PIT) of the surfactant ($S_1$) is inferior to 50° C.

Preferably, the surfactant ($S_1$) is nonionic. Preferably, it comprises a polyoxyethylene moiety and is notably a polyoxyethylene $C_6$-$C_{18}$ fatty acid ester such as the POE-300-stearate.

Considering a ternary mixture composed of a light mineral oil ($O_2$), water and POE-300-stearate ($S_1$), the 100× water/(water+oil) weight ratio is preferably comprised in the range of 30 to 90 and/or the ($S_1$) surfactant amount is in the range of 5 to 15 weight percent relative to the total weight of the ternary mixture, and preferably in the range of 8 to 13.

Step $i_1$)

In step $i_1$) of the PIT method applied to preparation of w/o nanoemulsion ($E_1$), the ternary mixture {water/non volatile oil ($O_2$)/surfactant ($S_1$)} is structured into a nanostructured bicontinuous system, which is an intermediary stage thermodynamically and kinetically very stable.

As used herein, the terms "nanostructured bicontinuous system" means that both the oil and water phases coexist in interconnected continuous domain with surfactant molecules located at the interface. These nanostructured bicontinuous systems are also called "Winsor IV bicontinuous microemulsions".

The temperature cycling consists essentially in increasing the temperature above the PIT, notably up to 30° C. above, and decreasing the temperature down to the PIT. For this reason, the PIT is preferably not superior to 70° C. This temperature cycling allows to form and to lead to the stabilization of the bicontinuous system. Further, the inventors have observed that the quality of the obtained nanoemulsion ($E_1$) is increased in terms of lowering the droplet diameter and polydispersity index (PDI) along with the number of cycles.

The heating and cooling rates of the temperature cycling are not critical and may vary in a wide range. They indeed only have an influence on the number of cycles necessary to form the nanoemulsion $E_1$. As an example, when using an heating and cooling rate of dT/dt=±1.5° C./min, six cycles, even three cycles may be sufficient to obtain a nanoemulsion $E_1$ having a low polydispersity index.

The temperature cycling being achieved with a chosen number of cycles, the obtained bicontinuous system is stabilized at a temperature near the PIT, preferably still under moderate stirring.

It should be noted that when the process is applied to the preparation of compositions having nanocapsules comprising a shell composed of an amphiphilic substance, such amphiphilic substance may alternatively be added at the beginning of step i1), instead of being added in step ii).

Step $i_2$)

Thereafter, in step $i_2$), the bicontinuous system which already shows a translucent and bluish aspect at this given temperature, is suddenly diluted with a volatile oil $O_1$ and the w/o nanoemulsion $E_1$ is immediately and irreversibly generated. The continuous phase is now actually a mixture of volatile oil $O_1$ and non volatile oil $O_2$.

It is to be noted that the stirring of the bicontinuous system during the dilution step as well as the stirring rate, do not influence the mechanism of nano-droplets formation, but allows to improves and insures the homogenization of the middle, thereby obtaining nanoemulsion having notably low polydispersity index.

According to this method, the volatile oil $O_1$ is preferably one having a viscosity lower than water such as pentane or isopentane.

Generally, a volume of $O_1$ at least equal to twice the bicontinuous system volume is added to generate the w/o nanoemulsions ($E_1$).

This volatile oil $O_1$ will interpenetrate the interconnected bicontinuous domain all the more quickly that its viscosity is low relative to water, thus generating the emulsion water-in-oil ($E_1$).

Step $i_3$)

The PIT method according to the invention may also comprise the addition of a further amount of a surfactant ($S_2$) in a step $i_3$). Indeed, it has been observed that the addition of further surfactant within the nanoemulsion continuous oil phase irreversibly results in stabilizing the suspension, that is, in preventing the aggregation process of the droplets.

Preferably, for insuring a good stabilization of the droplets, the further amount of surfactant ($S_2$) represents 30% to 40% by weight of the total surfactant amount.

The surfactant molecules ($S_2$) are assumed to wrap and coat the aqueous droplets, thereby inducing a steric stabilization between them.

The additional surfactant ($S_2$) may be identical or different to ($S_1$) implemented in step $i_1$).

Preferably, the surfactant ($S_2$) is more soluble in the oil phase than in the water phase. The surfactant ($S_2$) may be notably a polyoxyethylene fatty acid such as POE 300 stearate.

Step ii)

The aqueous droplets of the emulsion ($E_1$) thus formed after the end of step i) may optionally be reinforced by a "shell", before step iii).

In the context of the present invention, "shell" means a layer surrounding the aqueous droplet and which allows to reinforce the aqueous droplet stability.

Thus, in optional step ii) of the method, the interface of the emulsion ($E_1$) droplets is reinforced by a bidimensional network of polymer, or by an amphiphilic substance.

In a preferred aspect, the droplets of the emulsion ($E_1$) are reinforced by a polymer.

According to a preferred embodiment, the monomer is reactive with the aqueous phase so as to initiate the interfacial polymerization, soluble in the oil phase, i.e. more soluble in the oil phase than in the water phase, and/or non reactive with the surfactant(s) ($S_1$) and/or ($S_2$), or any other compound which is present in the emulsion $E_1$.

Preferably, the monomer comprises two diisocyanate (—N=C=O) groups. As examples of monomer, mention may be made of tolylene-2,4-diisocyanate (TDI), isophorone diisocyanate or 4,4-methyl-bis(phenylisocyanate). Most preferably, the monomer is tolylene-2,4-diisocyanate (TDI).

Without wishing to be limited to a theory, it is assumed that an isocyanate function of a monomer molecule, on contact with a water droplet, gives rise to the formation of an amine group, which afterwards is more reactive than water and preferentially reacts with another isocyanate monomer, thereby forming a polyurea. Thus, since the chemical reaction is a stepwise polymerization, and since the polyurea chains need, for growing, to be continuously on contact with both water and oil (monomer reservoir), the resulting thickness of the polymer shell is advantageously in the molecular range, and forms a grid-like interfacial network.

Advantageously, it has been observed that the polymer "grid" density may vary according to the monomer concentration. The higher the monomer content, the closer the formed polymer "grid". Thus, for the encapsulation of big hydrophilic molecules, a lower concentration of monomer will be needed than for the encapsulation of smaller ones.

Preferably, the concentration of monomer in the oil phase of the emulsion ($E_1$) is superior to 0.05 mg·$L^{-1}$ and notably superior to 0.5 mg·$L^{-1}$ and ranges notably from 0.6 to 0.8 mg·$L^{-1}$.

In another particular embodiment, the droplets of the emulsion ($E_1$) are reinforced by an amphiphilic substance.

The amphiphilic substances include notably surfactants, synthetic or biological polymers.

As used herein, the terms "biological polymer" are understood to mean a molecule found in nature, comprising more than 30 monomer units, typically comprising up to hundred of individual monomer units. Monomer units may be notably sugars, amino acids and nucleotides.

In the context of the present invention, the terms "biological polymer" also include the "bio-oligomers" which comprise 30 or less monomer units.

As examples of biological polymers, mention may be made of peptides, proteins (globular or fibrous) such as collagen (amino acid monomers), polysaccharides such as cellulose, alginate or chitine (sugar monomers), nucleic acid such as RNA and DNA (nucleotide monomers).

As used herein, the term "synthetic polymer" refers to a large molecule typically comprising up to thousand individual monomer units which may be identical or different. Thus, the terms "synthetic polymer" include homopolymers or copolymers. In the context of the present invention, the synthetic polymers may include surfactants.

Preferably, the amphiphilic substance is a surfactant $S_4$, notably a nonionic surfactant.

Preferably, the surfactant has an Hydrophilic Lipophilic Balance (HLB) superior or equal to 10.

Preferably, the surfactant $S_4$ is a polysorbate, most preferably polysorbate 80.

Step iii)

At this stage, the system obtained in optional step ii) comprises polymeric shell aqueous core nanocapsules (NC), dispersed in a mixture of volatile oil $O_1$ and non volatile oil $O_2$. Alternatively, the system obtained in step ii) comprises aqueous core nanocapsules (NC) having a shell composed of an amphiphilic substance.

According to another embodiment, at this stage, the system comprises aqueous droplets of emulsion ($E_1$) dispersed in a mixture of volatile oil $O_1$ and non volatile oil $O_2$.

In step iii), the composition of particles (P) is obtained by adding a volume of water, representing preferably 4 to 5 times the volume of the dispersion obtained at step ii) or i) and by removing, preferably simultaneously, the volatile oil $O_1$, notably through evaporation, by heating at a temperature superior to the boiling point of $O_1$ and preferably superior to 20° C. of the boiling point of ($E_1$).

Without wishing to be limited to any theory, a hypothesis which makes it possible to explain the formation of the lipid shell aqueous core particles (P) is that the energy provided to remove, notably to evaporate, the volatile oil enables a good homogenization of the system, and more specifically when the amount of volatile oil becomes very low. The non volatile oil $O_2$ spreads over the nanocapsules (NC) initially present in the oil phase, thereby obtaining small aqueous core lipid shell particles (P). Thus, the size of the particles (P) may advantageously be adapted according to the residual amount of non-volatile oil ($O_2$).

Further, it has been observed that as long as the volatile oil $O_1$ evaporates, that is the volume of the oil phase decreases, the surfactant ($S_1$) which is soluble in the oil phase, gradually crystallizes in the oil phase, notably in $O_2$. Finally, the solid surfactant ($S_1$) is enclosed in the oil phase which surrounds the droplets, thus forming a matricial lipid shell comprising amorphous solid surfactant and oil ($O_2$) wrapping the aqueous core optionally protected by the polymeric shell or by the amphiphilic substance (NC).

Step iv)

According to a preferred aspect, the method further comprises the step iv) of adding a hydrophilic surfactant ($S_3$) in the water phase. This additional step indeed advantageously allows to stabilize the obtained particles (P) and to prevent their aggregation.

As used herein "hydrophilic surfactant" means a surfactant having a "Hydrophilic Lipophilic Balance" (HLB) superior to 12, and more particularly to 14.

As an example of suitable hydrophilic surfactant ($S_3$), the POE 660 hydroxystearate (Solutol HS15®) may be cited, which has an HLB comprised between 14 and 16.

Alternatively, the method may also comprise an additional step consisting in further diluting the composition obtained in step iii) with water.

Encapsulation of Hydrophilic and/or Lipophilic Substances

The particles (P) obtainable by the method according to the invention may incorporate either a hydrophilic, or a lipophilic substance or both.

Hydrophilic and lipophilic substances may be notably selected from pharmaceutical, diagnostic, cosmetic, veterinary, phytosanitary products, or processed foodstuffs.

Hydrophilic substances may be incorporated in step i) of the method, more specifically in the water phase intended to form the nanostructured bicontinuous system.

Preferably, an aqueous solution containing an hydrophilic substance is added after the formation of a bicontinous system according to step $i_1$), prior to the addition of volatile oil $O_1$ according to step $i_2$). Accordingly, the temperature treatment to which the ternary mixture {non volatile oil ($O_2$)/water/surfactant ($S_1$)} is subjected to form the bicontinuous system does not affect advantageously the hydrophilic substance to be encapsulated.

The volume of the added aqueous solution is preferably very low, and may notably represent 1 to 5% by volume relative to the volume of the bicontinuous system. Thus this concentrated solution will very rapidly integrate the aqueous part of the bicontinuous system and the nanoemulsion $E_1$ will be generated identically after dilution with the volatile oil $O_1$ according to step $i_2$).

As regards lipophilic substances, they are preferably added after the interfacial polymerization step ii) and before step iii). Thereby, after the complete volatile oil evaporation, the lipophilic substances are equally shared onto the oil phase of particles (P).

According to a further object, the invention is directed to a composition comprising in an aqueous phase, particles (P) having a diameter in the range of 20 to 500 nm, said particles containing:
 an oil phase;
 in said oil phase,
 an aqueous droplet, or
 a nanocapsule (NC) comprising:
  an aqueous core, and
  a polymeric shell or a shell composed of an amphiphilic substance; and
 a surfactant.

This composition is obtainable according to the method of the invention.

In one aspect of the invention, the particles (P) contain in the oil phase, an aqueous droplet, optionally comprising an hydrophilic substance. This embodiment is particularly suitable for encapsulating various hydrophilic substances, notably having a high molecular weight.

Examples of such hydrophilic substances include notably proteins, plasmids, antibodies, polysaccharides.

In a further aspect, the particles (P) contain in the oil phase, a nanocapsule (NC) which comprises an aqueous core and a shell.

According to one aspect, the nanocapsule (NC) comprises a shell composed of an amphiphilic substance.

In a preferred aspect, the nanocapsule (NC) comprises a polymeric shell.

Preferably, the polymeric shell is composed of a polyurea.

Preferably, the nanocapsules (NC) of the particles (P) have a diameter in the range of 10 to 400 nm, and notably of about 50 nm, as determined by virtue of a particle size measurement performed on Transmission Electron Microscopy (TEM) and/or on Cryo-TEM.

Preferably, the aqueous core contains a hydrophilic substance.

Preferably, the oil phase contains a lipophilic substance.

Advantageously, the compositions according to the invention are characterized by a polydispersity index inferior to 0.5, notably of about 0.1.

According to a further object, the invention relates to a water-in-oil (w/o) emulsion ($E_1$) obtainable according to a method comprising the steps of:
 $i_1$) forming a nanostructured bicontinuous system from a mixture comprising:
  a non volatile oil ($O_2$);
  water; and
  a surfactant ($S_1$)
 by carrying out a temperature cycling around the PIT; and
 $i_2$) adding a volatile oil ($O_1$), thereby forming a w/o emulsion ($E_1$) wherein droplets have a hydrodynamic mean diameter in the range of 10 to 400 nm; and
 $i_3$) optionally adding a further amount of a surfactant ($S_2$), wherein the non volatile oil ($O_2$) is paraffin oil, and the volatile oil ($O_1$) is pentane or isopentane.

In a still further object, the invention concerns a water-in-oil (w/o) emulsion ($E_1$) comprising:
 as a continuous phase, isopentane or pentane as a volatile oil, and paraffin oil as a non volatile oil;
 as a discontinuous phase, water; and
 a surfactant ($S_1$)

Preferably, the surfactant ($S_1$) comprises a polyoxyethylene moiety.

These emulsions ($E_1$) are particularly advantageous as they display a good stability, thus enabling the preparation of stable compositions of particles (P) according to the invention.

According to a further object, the invention relates to the use of the compositions of particles (P) according to the invention for encapsulating a hydrophilic and/or a lipophilic substance.

FIGURES

FIG. 1: Schematic of the method of preparation of the compositions of particles (P) according to the invention. The polycondensation time, tp, is fixed in the process at 2 h.

Figure 2:
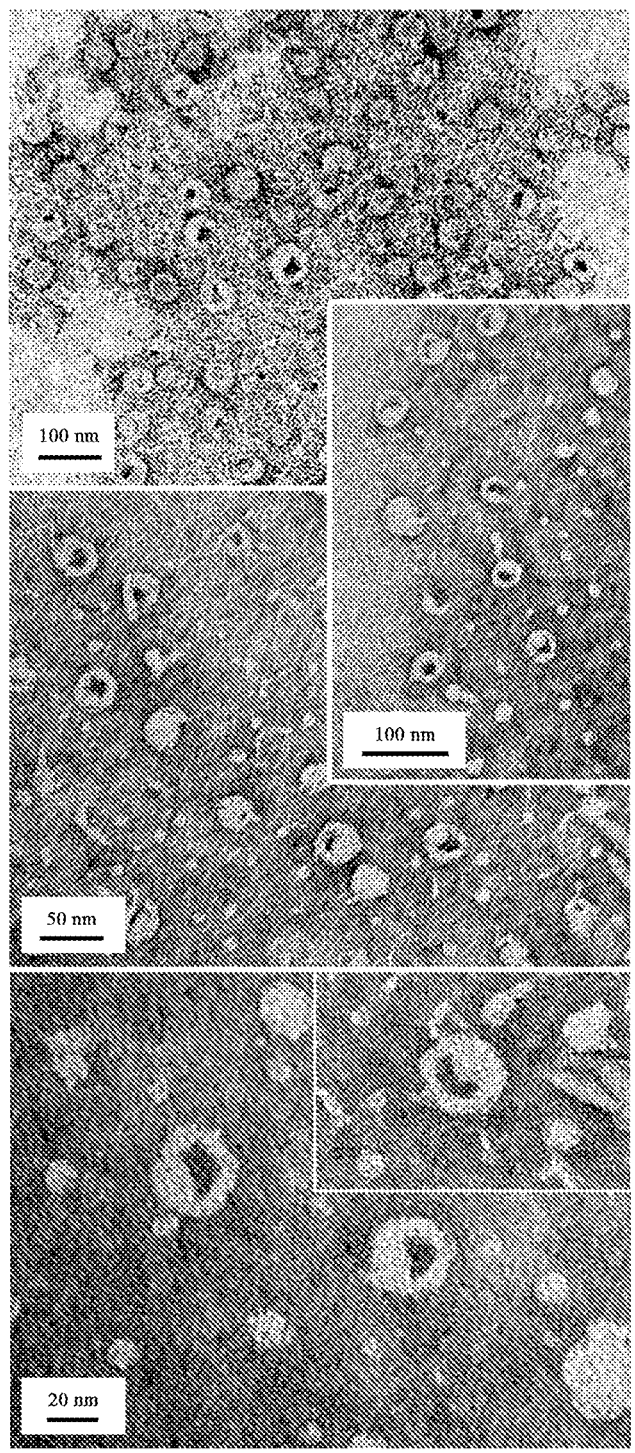

FIG. 2: TEM coupled with a negative staining technique (staining agent: uranyl acetate), of a diluted (1/10) sample of a composition of particles (P) according to the invention.

Figure 3:
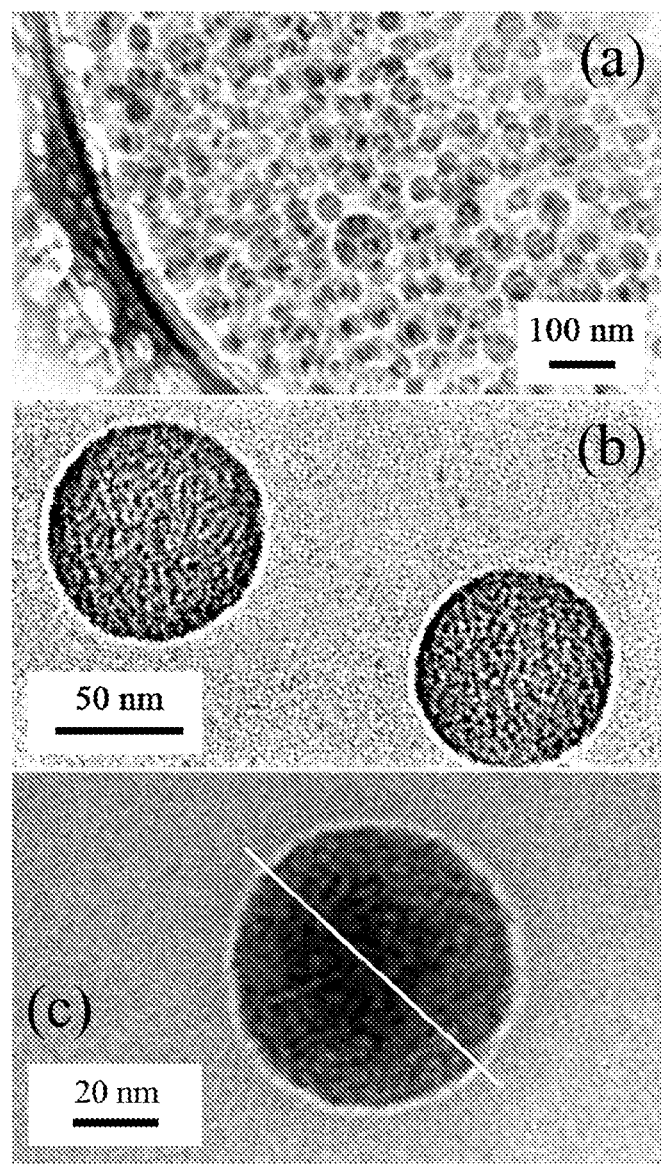
Figure 3:
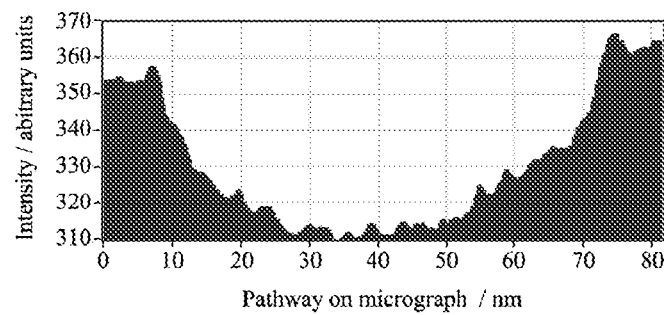

FIG. 3 (a) (b), (c): Cryo-TEM of a diluted (1/10) sample of a composition of particles (P) according to the invention and detail of electronic intensity following the pathway indicated in (a), (b), (c).

Figure 4:
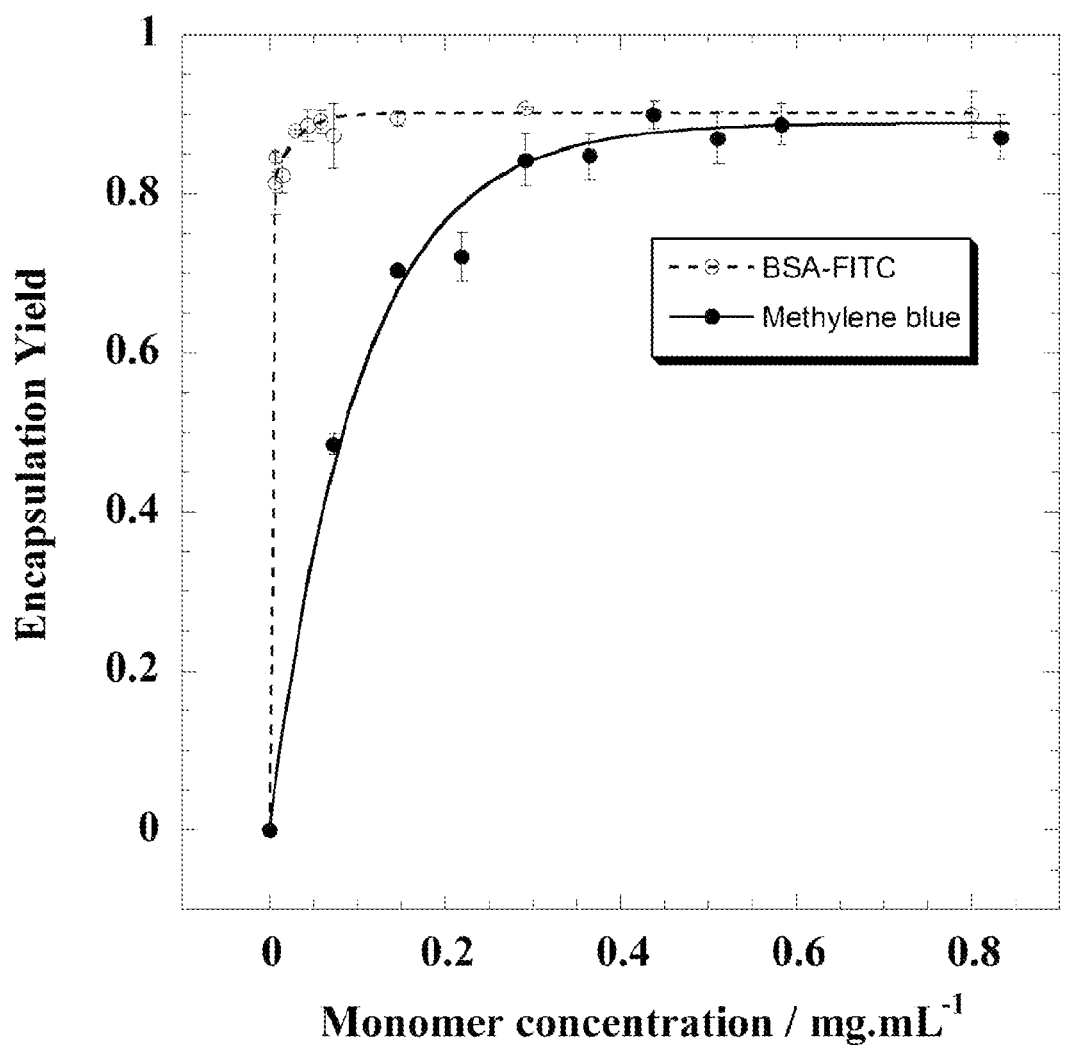
Figure 5:
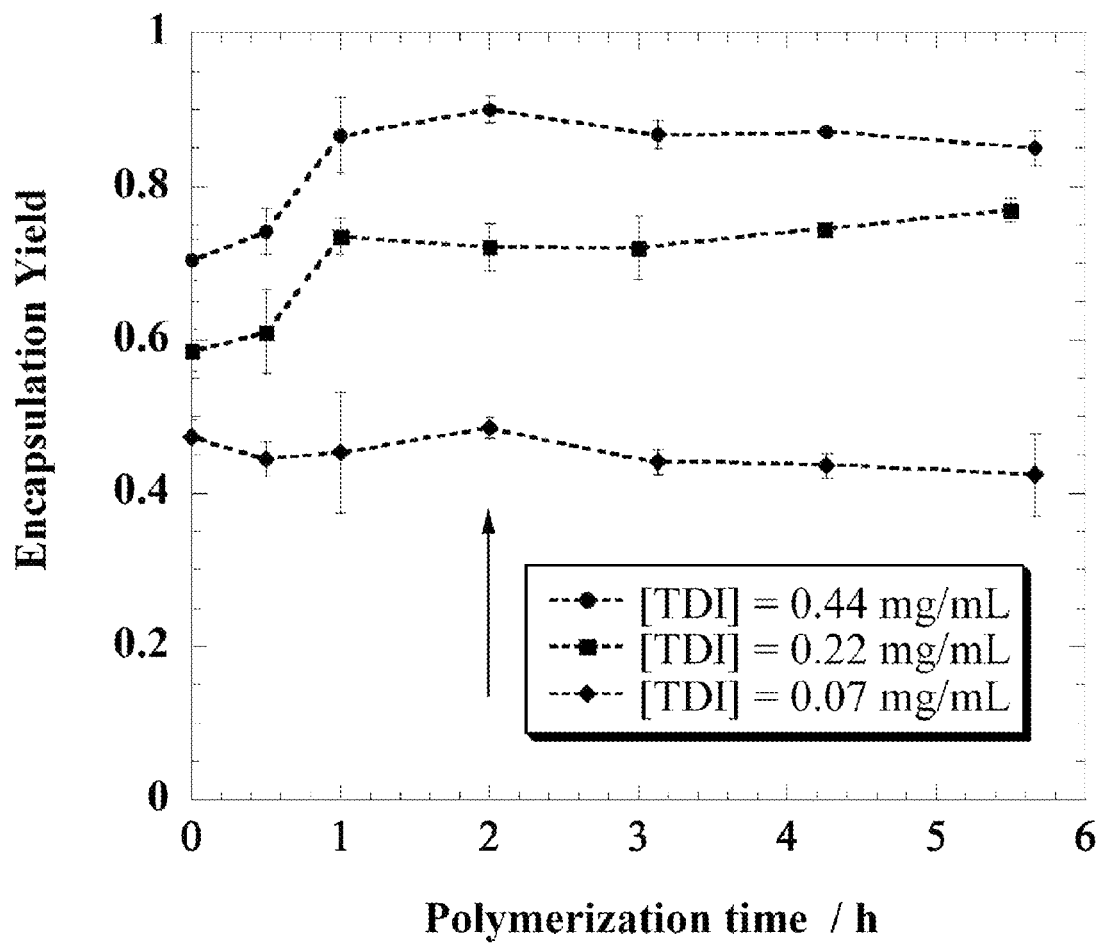

FIGS. 4 and 5: Influence of the formulation parameters on the encapsulation yields of hydrophilic molecules.

FIG. 4: Effects of the quantity of added monomer in the formulation, comparison between Methylene Blue (MB) and BSA-FITC, the polycondensation time $t_p$ is fixed at 2 hours.

FIG. 5: Effects of $t_p$ for MB, at three different monomer amounts, 0.07, 0.22, and 0.44 mg·mL$^{-1}$. The arrow indicates the selected time in the whole process of particles (P) preparation.

Figure 6:
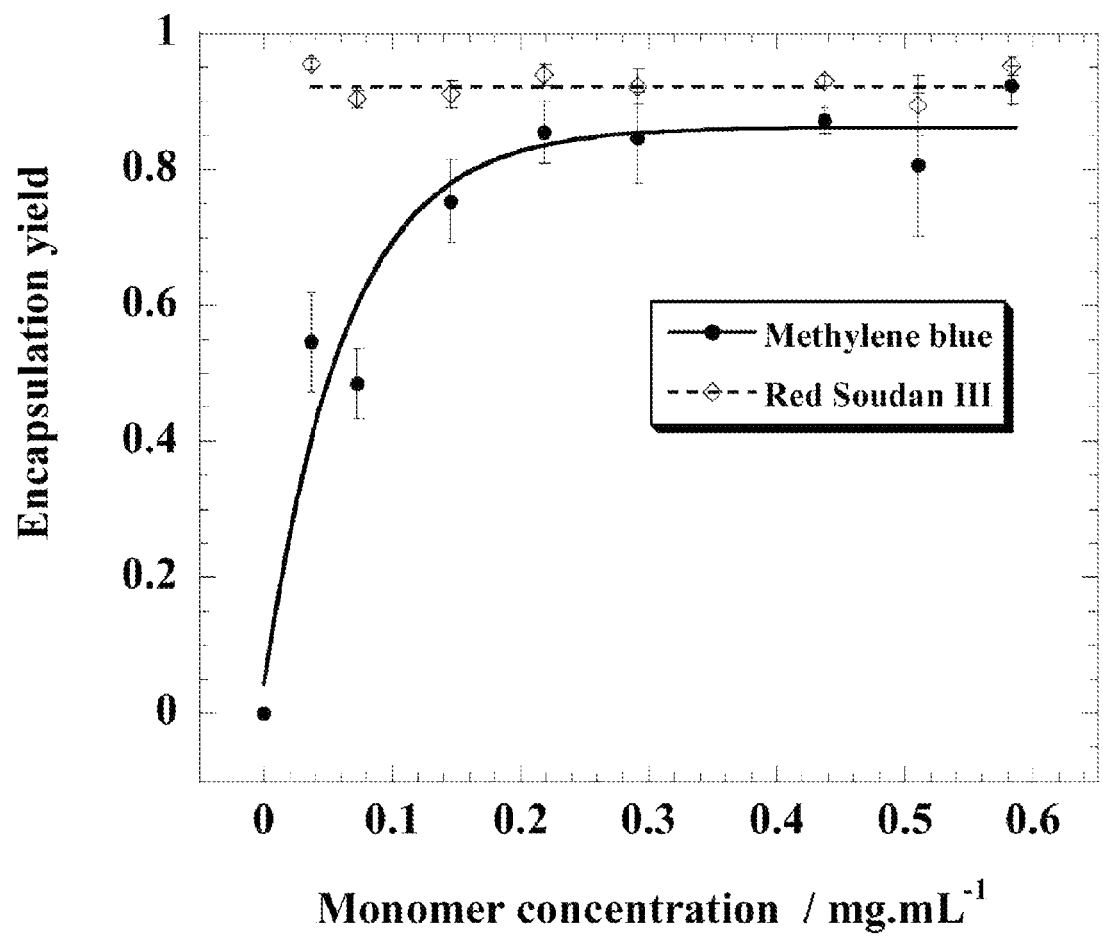

FIG. 6: Influence of the monomer content on the encapsulation yields of simultaneously encapsulated hydrophilic (Methylene Blue (MB) and lipophilic (Red Soudan (RS)) molecules. The polycondensation time $t_p$ is fixed at 2 hours.

Figure 7:
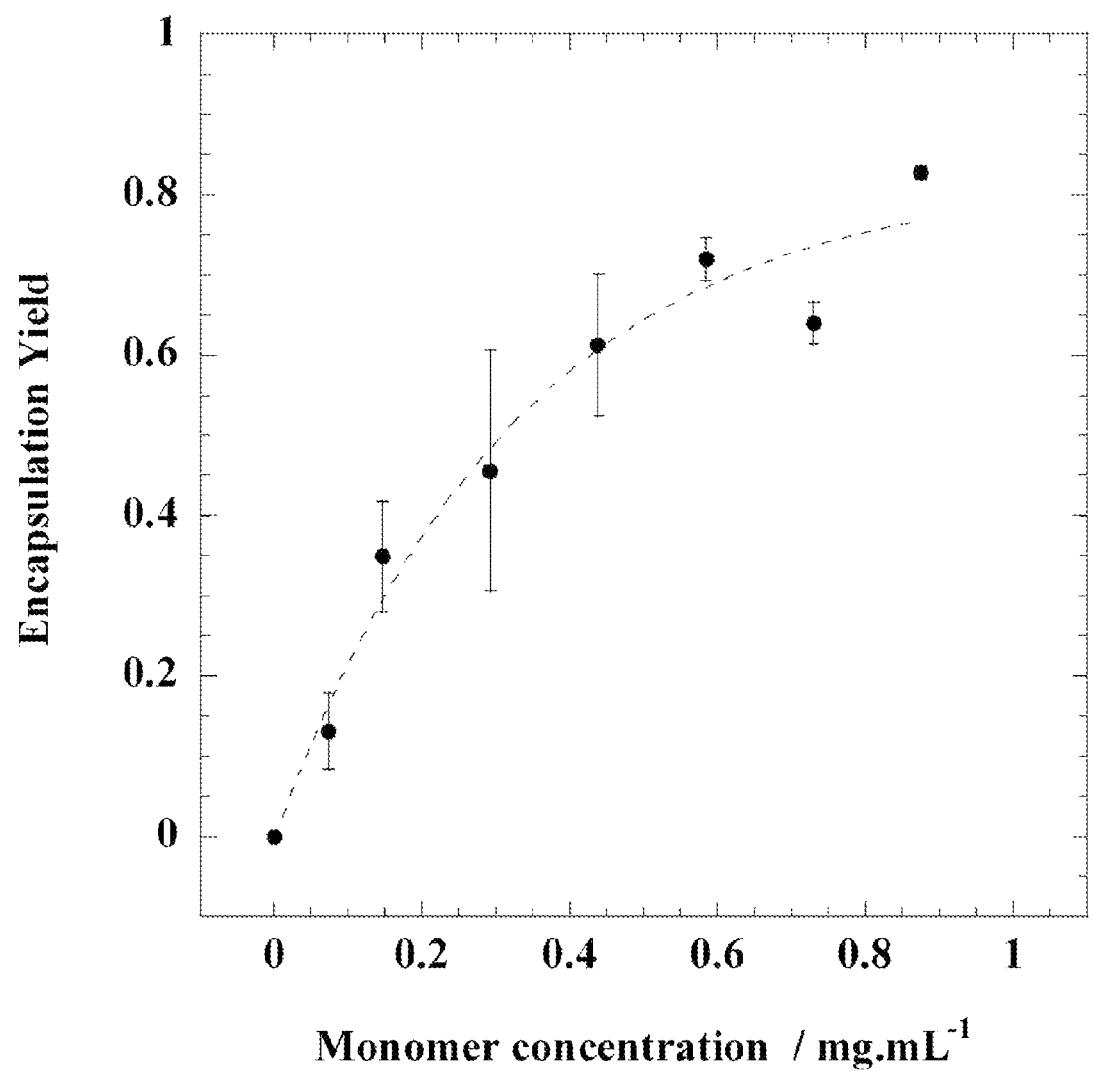

FIG. 7: Influence of the monomer content on the encapsulation yield of Chlorhydrate Doxorubicine (DOX).

Figure 8:
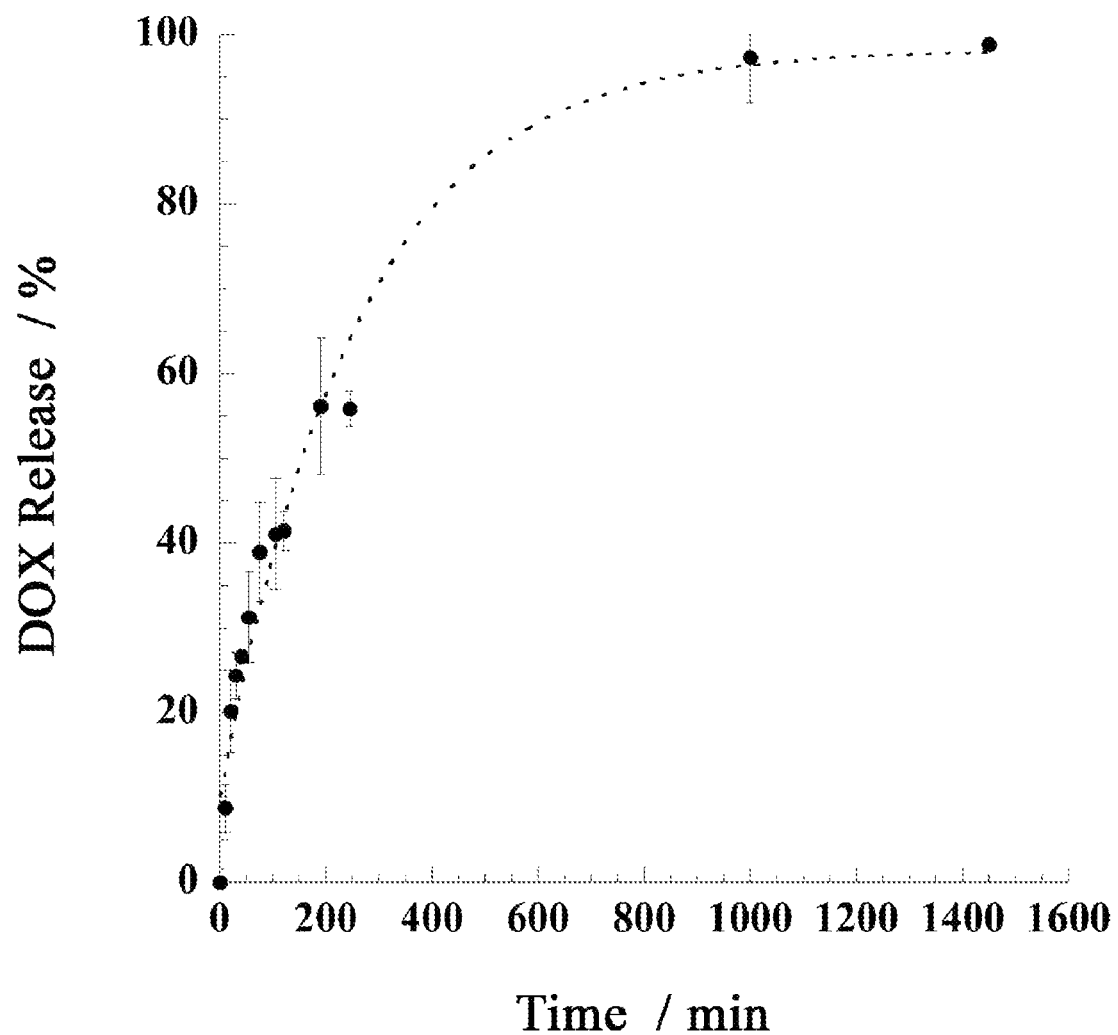

FIG. 8: Kinetic of Doxorubicine Chlorhydrate release from particles (P).

EXAMPLES

1. Materials and Methods 1.1. Materials

A technical grade polyethoxylated surfactant C18E6 was kindly furnished by Stearinerie-Dubois (Boulogne, France). It is a typical commercial product with a Poisson-like ethylene oxide (EO) distribution around six. This rather lipophilic amphiphile, i.e. presenting a low EO number, will stabilize the emulsions composed of 'light mineral oil' and water plus electrolyte (NaCl). Light mineral oil was purchased from Cooper (Melun, France), and it is a standardized denomination to refer to a mixture of saturated hydrocarbons obtained from petroleum. Ultrapure water was obtained by MilliQ® filtration system (Millipore, Saint-Quentin-en-Yvelines, France) and sodium chloride from Prolabo (Fontenay-sous-Bois, France). Finally, a very fluid and volatile apolar phase was also used as a second oil, and also as a key of the process: Isopentane (2-methylbutane) was obtained from Riedel-de-Han (Germany), which shows a absolute viscosity at 25° C., $\eta$ is.=0.35 mPa·s, and a boiling point $B^{is.}_p$=28° C.

Methylene Blue (MB), Bovine Serum Albumin-Fluorescein Isothiocyanate labeled (BSA-FITC), Red Soudan (RS) were purchased from Sigma.

1.2. Preparation of a Composition of Particles (P)

A composition of particles (P) was prepared according to the following general procedure on the basis of the following ingredients (table 1).

TABLE 1

| | Amounts |
|---|---|
| Microemulsion preparation | |
| NaCl | 0.8 g |
| MilliQ water | 26.88 g |
| Paraffin oil | 40.32 g |
| POE 300 stearate | 7.46 g |
| Nanoemulsion preparation ($E_1$) | |
| POE 300 stearate | 0.4 g |
| Isopentane | 30 ml |
| Interfacial polycondensation | |
| Tolylene-2,4-diisocyanate | 0.7 mg/L in isopentane |
| Evaporation | |
| MilliQ water | 20 ml |

1.2.1. Water-in-Oil Nano-Emulsions ($E_1$) Preparation

Macroscopic emulsions composed of 'light mineral oil' and MilliQ water (100×water/(water+oil) weight ratio: WOR=40) plus NaCl (concentration in water: 0.51 M), were stabilized by a nonionic polyethoxylated (PEO) surfactant with short PEO chain (PEO-300 stearate, 10 wt. %). PEO-300 stearate is given freely soluble in such "light mineral oil" and insoluble in water (Yu, C. D., 1994).

This system is definitively able to undergo an emulsion phase inversion as a function of the temperature (Salager, J. L. et al., 2004; Anton, N. et al., 2007). This phenomenon, the influence of the formulation and composition parameters, as well as this ternary system characterization has been studied in depth in previous studies (Anton, N. et al., 2007). Thus, when the system is precisely maintained at the temperature of emulsion phase inversion (PIT), a bicontinuous microemulsion (Winsor IV-like) spontaneously forms exhibiting a bluish and translucent aspect, structured at the nanometric scale (Kahlweit, M. et al., 1985; Forster, T. et al., 1995; Morales, D. et al., 2003; Izquierdo, P. et al., 2004). Next, a temperature cycling treatment is carried out around the PIT (35<T<60° C.), in order to 'structure' the transitional microemulsion, gradually increasing the fineness of the nanometric-scaled network along with the number of temperature cycles.

As a last step, this nanometric bicontinuous system at the PIT is suddenly diluted with another oil (isopentane), very fluid as compared as water. The water-in-oil nanoemulsions are immediately generated, typically exhibiting a droplet hydrodynamic diameter of ~40 nm and a very satisfactory polydispersity index of ~0.05 (measurements performed using a Nano ZS Malvern Instruments). Destabilization mechanisms of such w/o nanoemulsions has been shown to follow a colloidal aggregation process, typical of inverted emulsions for which inter-droplets interaction profile generally presents a deep primary minimum.

Further, it has been observed that, after having established the nanoemulsion, the addition of further surfactant within the nanoemulsion continuous oil phase (also the POE-300 stearate), irreversibly results in stabilizing the suspension, that is, in preventing the aggregation process. Practically, for insuring a good stabilization of the droplets, a surfactant amount which corresponds to ~35 wt. % of the total surfactant quantity is added. The nonionic surfactant molecules are assumed to wrap and coat the aqueous droplets, thereby inducing a steric stabilization between them.

1.2.2. Interfacial Polycondensation

The interfacial polycondensation stage is a stepwise process creating a bidimentional polyurea film onto the w/o nanoemulsion template. The criteria met by the chosen monomer was (i) a free solubility in the continuous oil mixture (isopentane plus mineral oil), and (ii) a good reactivity with the dispersed aqueous phase: The tolylene-2-4-diisocyanate (TDI), see FIG. 1, was chosen in this embodiment. In that way, an isocyanate function of a monomer molecule, on contact with a water droplet, will give rise to the formation of an amine group, which afterwards is more reactive than water and will preferentially react with another TDI molecule.

Thus, since the chemical reaction is a stepwise polymerization, and since the polyurea chains need, for growing, to be continuously on contact with both water and oil (monomer reservoir), the resulting thickness of the polymer shell will be in the molecular range, and forms an interfacial network which could be imagined as a grid (a concept that will be supported by the following results regarding the encapsulation yields). It is assumed that the reactions between monomer and potential $NH_2$ groups of molecules to be encapsulated will not interfere with the formation of the polymer film. The effects of the polycondensation time, tp, on the encapsulation yields are investigated below, and are eventually fixed at 2 hours for an optimized formulation.

1.2.3. Fabrication of Nanocapsules (NC)

At this stage, the experimental system is composed of aqueous nano-droplets, surrounded by a polyurea bidimentional film assumed to exhibit a grid-like structure, and dispersed in a bulk oil mixture of isopentane (from the PIT dilution) and of mineral oil (from initial emulsions). In addition, it is also to consider the potential presence in oil of some monomer molecules which have not reacted yet.

So, the generation of aqueous core nanocapsules (see FIG. 1) are achieved simply (i) by adding an additional water phase which will be the external one, and simultaneously (ii) by removing the isopentane phase through its own evaporation, one hour in a boiler at a temperature fixed significantly above the isopentane boiling point ($B^{is}_p$=28° C.), for instance at 50° C.

Thereby, the energy provided during this evaporation stage not only allows a rapid removing of the volatile oil, but also it ensures a suitable homogenization of the sample which will prevent the immediate droplets aggregation whilst the global oil volume is decreasing. The aqueous droplets may likely be equally spread out over the apolar phase, leading to the generation of distinct colloidal objects in water. In that way, owing to the presence in the apolar phase of the non-volatile mineral oil, it will be, when the isopentane evaporation is completed, finally shared out onto the newly-formed colloidal particles. Moreover, since the PEO nonionic surfactant used is totally insoluble in water, along with the oil evaporation, that is, the oil volume decrease, the amphiphiles will gradually crystallize in oil. Finally, the solid surfactant will be enclosed in the resulting mineral oil which surrounds the droplets, and therefore creates a matricial lipid shell made of amorphous solid surfactant and mineral oil wrapping the aqueous core protected by the polymer film (a structure illustrated in FIG. 1). This capsular structure is well supported by the below electron microscopy experiments, and also by their high ability to encapsulate simultaneously hydrophilic and lipophilic molecules. Finally, as regards the free monomers potentially remaining in oil, it appears that they were definitively neutralized (since also enclosed in the mineral oil) either on contact with the formed polymer film (by the terminal $NH_2$ groups), or with the external water phase.

1.2.4. Characterization of Nanocapsules (NC)

Microscopy Observations

Transmission electron microscopy (TEM). A drop of each aqueous dispersion specimen was first placed on a carbon-coated TEM copper grid (Quantifoil, Germany) and let to air-drying. The sample was then negatively stained with uranyl acetate (Merck, Germany). For that, the sample-coated TEM grid was successively placed on a drop of an aqueous solution of uranyl acetate (2 wt. %) and on a drop of distilled water. The grid was then air-dried before introducing them in the electron microscope. The samples were viewed using a JEOL JEM-1230 TEM operating at 80 kV.

Cryo-TEM. The specimens for cryo-TEM observation were prepared using a cryoplunge cryo-fixation device (Gatan, USA) in which a drop of the aqueous suspension was deposited on to glow-discharged holey-type carbon-coated grids (Ted Pella Inc., USA). The TEM grid was then prepared by blotting a drop containing the specimen to a thin liquid layer of approximately 50-500 nm in thickness remained across the holes in the support carbon film. The liquid film was vitrified by rapidly plunging the grid into liquid ethane cooled by liquid nitrogen. The vitrified specimens were mounted in a Gatan 910 specimen holder (Gatan, USA) that was inserted in the microscope using a cryotransfert system (Gatan, USA) and cooled with liquid nitrogen. The TEM images were then obtained from specimens preserved in vitreous ice and suspended across a hole in the supporting carbon substrate. The samples were observed under low dose conditions (lower than 10 e·A2), at −178° C., using a JEM 1230 'Cryo' microscope (Jeol, Japan) operated at 80 kV and equipped with a LaB6 filament. All the micrographs were recorded on a Gatan 1.35 K×1, 04 K×12 bit ES500W Erlangshen CCD camera.

Surface Potential Measurement

As an image of the nanocapsule surface potential, $\zeta$ potential was assessed using a Nano ZS (Malvern Instruments). We used the Smoluchowski's model linking electrophoretic mobility and $\zeta$ potential. The Helium-Neon laser, 4 mW, operates at 633 nm, with the scatter angle fixed at 173°, at a constant temperature of 25° C. However, the study in depth of the surface properties through the soft particle analysis model (H. Ohshima, et al., 2006) has shown that encapsulated materials has no influence on the surface potential of these objects. It shows that encapsulated materials does not take part of the shell structure.

1.2.5 Incorporating Hydrophilic and Lipophilic Model Molecules

Regarding the whole fabrication process in FIG. 1, the incorporation of hydrophilic and lipophilic species will appear performed by different ways.

(i) Hydrophilic materials, eventually, have to be shared out into the w/o nanoemulsions water droplets, and it may be done right from the start included in the water phase of the macro-emulsions preparations. Another higher effective manner consists in injecting a very small volume (no more than 2% (v./v.)) of very concentrated aqueous solution, in the microemulsion maintained at the PIT, after the temperature cycling, and before the isopentane dilution. The droplet injected in the (still) stirred microemulsion, very rapidly integrates the aqueous part of the bicontinuous network. As a result of the oil dilution, the nanoemulsion immediately forms, allowing a very homogeneous dispersion in oil of the injected hydrophilic molecule. Incorporating the hydrophilic species through this original manner, eventually prevents the molecules degradation during processing potentially due to the temperature cycling treatment. The hydrophilic model molecules were chosen with very different molecular weight: The first one is a labile dye, methylene blue (MB), the second is a protein, the bovin serum albumin fluorescein isothiocyanate labeled (BSA-FITC) and the last one is a fluorescent compound, Doxorubicin Chlorhydrate (DOX), which is an anti-cancer drug.

(ii) On the other hand, the lipophilic species were introduced in the oil phase of the nanoemulsion, after the chosen time of polymerization (to maximally prevent the potential interactions with the monomer), and before the stage of isopentane evaporation. Thereby, after the complete isopentane evaporation, the lipophilic added materials will be equally shared onto the droplets enclosed in the residual mineral oil, that is, trapped in the amorphous oil/non-ionic surfactant matrix. It finally appears as a marker of the residual mineral oil location, and determining a significant encapsulation yield should support the proposed multi-functional water/oil structure. The lipophilic model molecule is also a dye, the red Soudan III (RS). It is important to note here, that these processes of nanocapsule formulation containing hydrophilic and lipophilic agents can be still considered as only involving a low quantity of energy (often called 'low-energy' methods). Thereby, encapsulated molecules are not subjected to 'high-energy' emulsifying processes and devices (such as high pressure homogenizer or sonifier) and not even to the temperature cycling. A potential degradation during processing, of the fragile molecules to be encapsulated, is prevented.

All the quantifications were performed following an indirect method, after separating the external water to the nanocapsules by centrifugation (30 min, 14500 rpm), it was freeze-dried (RP2V, SGD, Le Coudray Saint-Germer, France) to ensure the destruction of the potentially remaining nanocapsules (and also to prevent their additional light adsorption in the quantification process). Next, the freeze-dried samples are solubilized in dichloromethane (DCM), and the different incorporated molecules except DOX which are present in the external water are simply quantified using a Spectrophotometer UV-visible Uvikon 922 Spectrophotometer (Bio-Tek Koutron instruments, Saint-Quentin-en-Yvelines, France). DOX was quantified using a spectrofluorimeter (Fluoroskan Ascent FL, type 374, Thermo Electron Corporation, Finland). The excitation and emission light passes through the band-pass filters at 485 nm and 550 nm respectively.

1.2.6. Release Yield of Doxorubicin from Particles (P)

To establish the drug release kinetics (see FIG. 8), 2 mL of freshly prepared suspension containing DOX-loaded particle (P), enclosed into a dialysis 15 kDa membrane (Spectra/Por® Membranes, Fisher Bioblock Scientific, Illkirch, France), were added to 40 mL of phosphate buffered saline (PBS, pH 7.4) from Sigma. The flack was weakly mechanically stirred (125 rpm) in darkness, at 37° C. (in a boiler, Julabo SW22, JULABO Labortechnik GmbH, Seelbach, Germany). Next, 500 µL of release medium were collected at specified time points and the DOX concentrations were determined by spectrofluorimetry, as previously described. This collected volume was systematically replaced by the same volume of fresh PBS for insuring the "sink" experimental conditions.

2. Results 2.1 Nanocapsules Characterization

The negative stained TEM pictures of these aqueous-core nanocapsules are presented in FIG. 2, and the Cryo-TEM ones shown in FIG. 3. From these both complementary experimental techniques, it emerges complementary informations, and eventually, very consistent with the suggested structure FIG. 1. The first remark concerns the droplets size, which appears around 50 nm, and which is finally consistent (minus the oil plus surfactant shell thickness) with the measured w/o nanoemulsion size. Furthermore, the theoretical oil/surfactant shell thickness can be approached only considering the materials forming the nanocapsules, knowing their respective proportions, and assuming that the nanocapsules exhibits the assumed structure: it results a thickness around 7.5 nm. This calculated result seems also supported by the core/shell proportions presented in FIG. 2.

In addition, these electron microscopy pictures show a relatively good monodispersity of the capsules, and then attest a relatively good quality of the dispersion and of such a formulation process. Of course, the capsular structure with aqueous core of these colloidal objects is proved in FIG. 2 since the object have likely exploded during the measurement along the vacuum establishment stage. The cavities being then invested by the (hydrophilic) staining agent producing contrasted spots within the nanocapsules.

On the contrary, the Cryo-TEM pictures in FIGS. 3 (a), (b), (c) present intact nanocapsules, and likewise showing a capsular structure owing to the difference in contrast between the center and the border of the particles. Indeed, the difference between organic species and water is contrasted enough to appreciate such details without staining agents. Finally, regarding the detail of electronic intensity disclosed on FIG. 3, a certain shell texture that evidences the random distribution of the organic materials (and the polymer arrangement) into the nanocapsule shell. It is still coherent with suggested mechanism and grid-like structure shown in FIG. 1.

2.2 Stability

Owing to the particular nanocapsule structure, the presence of polymer constituting the shell framework, since the surfactant used has a short PEO-chain with regards to its lipophilic part and also since it is mostly crystallized in the oil shell, the repulsive contributions forces as much of electrostatic as of steric origins appear very low. The nanocapsules freshly-formed exhibit a very good monodispersity as well as a polydispersity index (from Nano ZS Malvern, in suitable dilution conditions) relatively good, that is, lower than 0.1. Then, the concentrated NC suspension is rapidly destabilized clearly through a colloidal aggregation process in water, showing after about one month storage a creamed concentration of NC. Indeed, when large enough (>1 µm), the clusters are subjected to the gravitational forced. On the other hand, this process is significantly reduced by simply diluting the samples (e.g. 1/100), and the suspensions appear stable for months.

2.3 High Efficient Nanoencapsulation of Hydrophilic and/or Lipophilic Molecules

Owing to the real challenge that constitutes the encapsulation of hydrophilic agent into nanocapsules themselves dispersed in aqueous continuous phase, the first result will concern the extent in which the selected hydrophilic species, methylene blue and BSA-FITC, can be encapsulated into such colloids. The molecules incorporation during the nanoemulsion generation step as well as the molecule quantification for determining the encapsulation yield, follow the above-described procedures. Thereby, the effects of the formulation parameters, the quantity of monomer introduced in the formulation, and the polymerization time $t_p$, on the encapsulation yield are disclosed in FIG. 4.

Therefore, for an optimized polycondensation time fixed at $t_p$=2 h, the FIG. 4 compares the effects of the monomer amount added within the w/o nanoemulsion, on the encapsulation yields, and for both different hydrophilic molecules MB and BSA-FITC. Thus, the trends appear very similar, from an impossible encapsulation with the absence of monomer where the yield is assumed to be null and the internal water totally escapes towards the external one, to very satisfactory yields at the highest monomer contents. The plateaus attained for both BM and BSA-FITC result very similar about 0.9, but the very interesting point appears in the shift which exists between the two molecules. Indeed, compared with the little dyes, the big proteins are retained for lower monomer amounts. The plateau is already attained around 0.05 mg·L$^{-1}$ for BSA-FITC whereas it is rather around 0.5 mg·L$^{-1}$ for MB, which could likely indicate that it exists a correlation between monomer concentration and polymer 'grid' density: the higher the monomer content, the closer the formed polymer 'grid'. Eventually, this result is coherent with the nanocapsules structure above-suggested, since the polycondensation reaction will only create a bidimensional film in which the polymer fibers are intergrown forming a 'grid-like' network. It follows therefrom that during the isopentane evaporation, the provided energy will induce a part of the encapsulated molecules to escape towards the external water, and likewise that, this escape is reduced as the polymer grid density is increased. Moreover, from the differences observed between MB and BSA-FITC, it appears that the molecular weight of the encapsulated molecule is also of importance in the process. The biggest molecules being more easily stopped by the polymer network than the smaller ones, up to they reach similar encapsulation yields (at ~0.5 mg·L$^{-1}$).

The FIG. 5 presents the effects of the polycondensation time $t_p$ on the encapsulation yield of MB, for three selected added quantity of monomer. So, $t_p$ corresponds to the delay between the monomer addition into the nanoemulsion, and the isopentane evaporation step. A time during which the sample is still weakly stirred, at 500 rpm. Its value fixed above in the process ($t_p$=2 h), is finally justified here, since it clearly appears that a certain stabilization is rapidly attained (less than 1 hour) similarly in each case. Furthermore, owing to the isopentane evaporation step in which the monomer will be enclosed in the thin oil layer (and forced to be on contact with either the internal water, the polymer shell, or the external water), all TDI molecules will finally be forced to react and join the polyurea network. In that sense, the differences of encapsulation yields given for short $t_p$, and thus for the same quantity of polymer synthesized, will be originated by the non-uniformly distributed polymer in the nanocapsule structure. It is even legitimate to conceive that this forced polycondensation (for short $t_p$) can create polymer holes in the capsule, by which the internal water can escape through the oil.

Now as regards the simultaneous encapsulation of hydrophilic and lipophilic components, the experiments incorporating methylene blue and red Soudan III within the same nanocapsules, were carried out and reported in FIG. 6. As above-tackled, the encapsulation yield is measured as a function of the monomer amount added in the formulation, and the optimized polycondensation time is chosen at 2 hours. Likewise, as beforehand suggested by the NC structure, MB is in the internal water and RS in the oily surrounding shell. Of course, the methylene blue curve exhibits a very similar aspect than the one shown in FIG. 4 for which it was alone in the nanocapsule. Regarding now the red Soudan III, it clearly appears that the monomer amount has no influence on its encapsulation yields, and eventually, it is coherent with the process since the lipophilic molecules are added in the oil phase after the interfacial polycondensation. As a result, the RS is enclosed in the oil/amorphous surfactant shell and presents a quite high encapsulation yield, so given around 0.92.

To summarize, these objects not only show an interesting ability to encapsulate hydrophilic species with a particular influence of the polymer inner framework, but also they present a significant ability to simultaneously encapsulate hydrophilic (MB) and lipophilic (RS) model molecules. These multifunctional properties appear relatively original since such objects include in their own structure liquid water and oil reservoirs, and likewise since they exhibit a size in the colloidal range.

A further aspect of this study has dealt with the follow-up of the DOX encapsulation yields in function of the formulation variables. Hence, a thorough study showed that only two parameters have a significant influence on the encapsulation yield: the monomer amount and the time let for the polycondensation (tp). Yields rapidly reach a plateau when tp exceeds about 1-1.5 h and whatever the concentration of monomer, we thus fixed in the process tp=2 h.

On the other hand, the influence of the monomer amount on the DOX encapsulation yield show a typical evolution presented in FIG. 7. This behavior discloses that the nanocapsules structure and the formation of homogeneous shell (without holes), are intimately linked to the monomer concentration, and therefore to the polymer compactness at the droplet interface. These results allow the process optimization by defining a compromise between encapsulation yield and whole amount of polymer.

Afterwards, release behavior of aqueous-core nanocapsules was investigated in physiological conditions, the results are presented in FIG. 8. They will not only provide information on shell permeability and DOX release mechanisms, but also on the structural properties of the aqueous-core nanocapsules. Eventually, they also confirm the DOX is effectively encapsulated within a capsule, and can entirely be released with time (up to ~100% given by the curve fit). It is to be noted in the first place, that the release profile has an exponential behavior, well fitted by an exponential function (R=0.992).

2.4. Cytotoxicity of Particles (P) without any Active Ingredient Encapsulated

The cytotoxicity of particles (P) prepared according to 1.2 hereabove—without any active ingredient encapsulated (hereafter called NCB)—was assessed on NIH/3T3 cells (fibroblasts of mice *Mus musculus*). The particles (P) were exposed to various particle concentrations, during 4, 24, 48 or 72 hours. The cell survival was determined by the MTT test. Results are reported in the table below and in FIG. 9. No significant toxicity was noticed for dilution up to ¹⁄₁₀₀₀.

| mean | control | DMSO | NCB 1/10 | NCB 1/100 | NCB 1/1000 | NCB 1/10000 |
|---|---|---|---|---|---|---|
| 4 H | 100.00 | 46.75 | 24.98 | 90.40 | 86.12 | 92.79 |
| 24 H | 100.00 | 10.22 | 9.20 | 40.06 | 84.58 | 102.73 |
| 48 H | 100.00 | 4.79 | 5.91 | 35.16 | 72.94 | 83.45 |
| 72 H | 100.00 | 5.00 | 6.00 | 51.00 | 98.00 | 111.00 |

| deviation | control | DMSO | 1/10 NCB | NCB 1/100 | NCB 1/1000 | NCB 1/10000 |
|---|---|---|---|---|---|---|
| 4 H | 11.91 | 9.03 | 5.17 | 1.18 | 10.13 | 6.84 |
| 24 H | 4.03 | 2.60 | 3.83 | 5.22 | 17.10 | 23.07 |
| 48 H | 22.70 | 1.35 | 2.60 | 13.79 | 11.25 | 12.55 |
| 72 H | 2.05 | 0.64 | 0.21 | 11.91 | 2.64 | 1.79 |

2.5. Preparation of a composition of particles (P) containing nanocapsules (NC) comprising a shell composed of Tween™ 80 as an amphiphilic substance.

The compositions were prepared according to the general method as set out above (see par. 1.2.1 and 1.2.3), on the basis of the following ingredients:

| | Amounts |
|---|---|
| Microemulsion preparation | |
| NaCl | 0.08 g |
| MilliQ water | 2.6 g |
| Paraffin oil | 4 g |
| POE 300 stearate | 0.74 g |
| Tween™ 80 | 0.124 g |
| Nanoemulsion preparation (E1) | |
| POE 300 stearate | 0.4 g |
| Isopentane | 30 mL |
| Evaporation | |
| MilliQ water | 20 mL |

3 temperature cycles were performed between 35 et 60° C., under stirring (500 rpm). During the cooling phase of the third cycle, the system was diluted at 50° C., by adding isopentane and POE 300 searate, the reby forming a stable (w/o) nanoemulsion.

The nanocapsules were then formed by adding the obtained nanoemulsion in milliQ water at 50° C. and evaporating isopentane during about 1 hour.

The stability over the time of the obtained composition was studied by monitoring the evolution of the size and of zeta potential of particles (P) (measured with a nanosizer ZS, see par. 1.2.4)

The results have shown a good stability of the particles corresponding to constant values of size and zeta potential versus time (one month).

2.6. Comparison of the encapsulation yield of an hydrophilic anticancer drug (doxorubicin), in the presence or in the absence of a monomer (encapsulation by aqueous droplets)

The compositions were prepared according to the general method as set out above (see par. 1.2.1 and 1.2.3), on the basis of the following ingredients:

|  | Amounts |
| --- | --- |
| Microemulsion preparation | |
| NaCl | 0.08 g |
| MilliQ water | 2.6 g |
| Paraffin oil | 4 g |
| POE 300 stearate | 0.74 g |
| Nanoemulsion preparation (E1) | |
| POE 300 stearate | 0.4 g |
| Isopentane | 30 mL |
| Evaporation | |
| MilliQ water | 20 mL |

3 temperature cycles were performed between 35 et 60° C., under stirring (500 rpm), thereby forming a microemulsion. This micremulsion was then stabilized at 39° C.

50 µL of a solution of doxorubicine in water (4.18 mg/ml), were then successively added to the microemulsion, thereby forming a w/o nanoemulsion loaded with doxorubicine after dilution with isopentane.

A portion of this nanoemulsion was then subjected to an interfacial polymerization with tolylene 2,4-diisocyanate (see par 1.2.2 above), while another portion was not.

The nanocapsules were then formed by adding the obtained nanoemulsion in milliQ water at 50° C. and evaporation of isopentane was performed during about 1 hour.

The size of the aqueous nanocapsules or aqueous droplets of these two nanoemulsions was 130 nm (measured with a nanosizer ZS).

The yield of encapsulated doxorubicin in polymeric nanocapsules was of 70% and in aqueous droplets of 30%.

These results demonstrate that aqueous droplets are able to encapsulate doxorubicine, even if lower encapsulation yields are reached in comparison to those obtained with polymeric nanocapsules.

REFERENCES

Hillaireau, H.; Le Doan, T.; Besnard, M.; Chacun, H.; Janin, J.; Couvreur, P., Int. J. Pharm. 2006, 324, 37-42.
Ruysschaert, T.; Paquereau, L.; Winterhalter, M.; Fournier, D., Nano Lett. 2006, 6,2755-2757.
Gomes, J. F. P. d. S.; Sonnen, A. F.-P.; Kronenberger, A.; Fritz, J.; Coelho, M. A. N.; Fournier, D.; Fournier-Noel, C.; Mauzac, M.; Winterhalter, M. Langmuir, 2006, 22, 7755-7759.
Yu, C. D., Handbook of Pharmaceutical Excipients, second edition; The Pharmaceutical Press: London, 1994.
Salager, J. L.; Forgiarini, A.; Marquez, L.; Pena, A.; Pizzino, A.; Rodriguez, M.; Rondon-Gonzalez, M., Adv. Colloid Interface Sci. 2004, 108-109, 259-272.
Anton, N.; Saulnier, P.; Beduneau, A.; Benoit, J. P., J. Phys. Chem. B 2007, 111, 3651-3657.
Shinoda, K.; Saito, H. J. Colloid Interface Sci. 1968, 26, 70-74.
Shinoda, K.; Saito, H. J. Colloid Interface Sci. 1969, 30, 258-263.
Kahlweit, M.; Strey, R.; Firman, P.; Haase, D. Langmuir 1985, 1, 281-288.
Forster, T.; von Rybinski, W.; Wadle, A. Adv. Colloid Interface Sci. 1995, 58, 119-149.
Morales, D.; Gutierrez, J. M.; Garcia-Celma, M. J.; Solans, C. Langmuir 2003, 19, 7196-7200.
Izquierdo, P.; Esquena, J.; Tadros, T. F.; Dederen, J. C.; Feng, J.; Garcia-Celma, M. J.; Azemar, N.; Solans, C. Langmuir 2004, 20, 6594-6598.
Ohshima, H., Electrophoresis of soft particles: Analytic approximations, Electrophoresis 27 (2006) 526-533.

The invention claimed is:

1. A composition comprising in an aqueous phase, particles having a diameter in the range of 20 to 500 nm, said particles comprising:
   a solid nonionic surfactant in an oil phase,
   said solid nonionic surfactant and oil phase forming a lipid shell wrapping an aqueous droplet or a nanocapsule (NC),
   said nanocapsule (NC) comprising an aqueous core, and a polymeric shell or a shell composed of an amphiphilic substance,
   wherein said composition presents a polydispersity index inferior to 0.5.

2. The composition of claim 1, wherein the nanocapsule (NC) comprises a shell composed of an amphiphilic substance.

3. The composition of claim 2, wherein the amphiphilic substance is a surfactant $S_4$.

4. The composition of claim 3, wherein the surfactant $S_4$ is a nonionic surfactant.

5. The composition of claim 4, wherein the surfactant $S_4$ has an Hydrophilic Lipophilic Balance (HLB) superior or equal to 10.

6. The composition of claim 5, wherein the surfactant $S_4$ is a polysorbate.

7. The composition of claim 1, wherein the nanocapsule (NC) comprises a polymeric shell.

8. The composition of claim 7, wherein the polymeric shell is composed of a polyurea.

9. The composition of claim 1, wherein the nanocapsules or aqueous droplets have a diameter in the range of 10 to 400 nm.

10. The composition of claim 1, wherein the aqueous core or aqueous droplets contains a hydrophilic substance.

11. The composition of claim 1, wherein the oil phase contains a lipophilic substance.

12. A method for preparing a composition according to claim 1, comprising the steps of:
   i) preparing a water-in-oil (w/o) emulsion ($E_1$) wherein droplets have a mean hydrodynamic diameter of 10 to 400 nm, wherein the continuous phase contains two oils, a volatile ($O_1$) and a non volatile oil ($O_2$), the volatile oil ($O_1$) being more volatile than water, and the non volatile oil ($O_2$) being less volatile than water;

ii) optionally forming aqueous core-shell nanocapsules (NC), either by adding a monomer which is soluble in the continuous phase of the emulsion ($E_1$) and which polymerizes when in contact with water or by adding an amphiphilic substance; and iii) adding a water phase and removing the volatile oil ($O_1$), thereby forming a composition according to claim 1.

13. The method of claim 12, wherein the emulsion ($E_1$) comprises a surfactant ($S_1$), which is more soluble in the non volatile oil ($O_2$) than in water when the temperature is superior to the phase inversion temperature (PIT) and more soluble in water than in the non volatile oil ($O_2$) when the temperature is inferior to the PIT, and wherein the water-in-oil (w/o) emulsion ($E_1$) is prepared according to a method comprising the steps of:

$i_1$) forming a nanostructured bicontinuous system from a mixture comprising:
the non volatile oil ($O_2$);
the water; and
the surfactant ($S_1$)
by carrying out a temperature cycling around the PIT;

$i_2$) adding the volatile oil ($O_1$), thereby forming a w/o emulsion ($E_1$) wherein droplets have a hydrodynamic mean diameter in the range of 10 to 400 nm; and $i_3$) optionally adding a further amount of a surfactant ($S_2$).

14. The method of claim 13, wherein an aqueous solution containing an hydrophilic substance is added to the obtained nanostructured bicontinuous system before step $i_2$).

15. The method of claim 13, wherein the surfactant ($S_1$) comprises a polyoxyethylene moiety.

16. The method of claim 15, wherein the surfactant ($S_1$) is a polyoxyethylene $C_6$-$C_{18}$ fatty acid ester.

17. The method of claim 16, wherein the surfactant ($S_1$) is a POE-300-stearate.

18. The method of claim 12, wherein the non volatile oil ($O_2$) is a light mineral oil.

19. The method of claim 12, wherein the volatile oil ($O_1$) is pentane or isopentane.

20. The method of claim 13, wherein the further amount of surfactant ($S_2$) represents 30% to 40% by weight of the total surfactant amount.

21. The method of claim 12, wherein the monomer comprises two diisocyanate groups.

22. The method of claim 21, wherein the monomer is selected from tolylene-2,4-diisocyanate, isophorone diisocyanate or 4,4-methyl-bis(phenyl-isocyanate).

23. The method of claim 12, wherein a lipophilic substance is added after the polymerization step ii) and before step iii).

24. The method of claim 12, wherein the hydrophilic and the lipophilic substances are selected from pharmaceutical, diagnostic, cosmetic, veterinary, phytosanitary products, or processed foodstuffs.

25. The method of claim 12, further comprising the step iv) of adding an hydrophilic surfactant ($S_3$) in the water phase after step iii).

* * * * *

UNITED STATES PATENT AND TRADEMARK OFFICE
CERTIFICATE OF CORRECTION

PATENT NO. : 9,522,121 B2  
APPLICATION NO. : 12/678868  
DATED : December 20, 2016  
INVENTOR(S) : Nicolas Anton et al.

Page 1 of 1

It is certified that error appears in the above-identified patent and that said Letters Patent is hereby corrected as shown below:

On the Title Page

In item (73), the assignee should be UNIVERSITE D'ANGERS, ANGERS (FR) AND INSTITUT NATIONAL DE LA SANTE ET DE LA RECHERCHE MEDICALE (INSERM), PARIS (FR)

Signed and Sealed this  
Thirtieth Day of May, 2017

Michelle K. Lee  
*Director of the United States Patent and Trademark Office*